United States Patent
Fuchs et al.

(10) Patent No.: US 8,052,991 B2
(45) Date of Patent: Nov. 8, 2011

(54) METHOD OF PREPARING AN UNSATURATED FATTY ACID DRY CONCENTRATE

(75) Inventors: Norbert Fuchs, Mariapfarr (AT); Peter Kössler, Mariapfarr (AT)

(73) Assignee: VIS-Vitalis Linzenz-Und Handels GmbH, Anif (AT)

( * ) Notice: Subject to any disclaimer, the term of this patent is extended or adjusted under 35 U.S.C. 154(b) by 1906 days.

(21) Appl. No.: 10/312,077

(22) PCT Filed: Jun. 19, 2001

(86) PCT No.: PCT/AT01/00197
§ 371 (c)(1),
(2), (4) Date: Apr. 14, 2003

(87) PCT Pub. No.: WO01/97634
PCT Pub. Date: Dec. 27, 2001

(65) Prior Publication Data
US 2003/0157175 A1    Aug. 21, 2003

(51) Int. Cl.
*A61K 47/00* (2006.01)
*A61K 9/14* (2006.01)
(52) U.S. Cl. ............... 424/439; 426/99; 424/489
(58) Field of Classification Search ........... 424/470; 426/302
See application file for complete search history.

(56) References Cited

U.S. PATENT DOCUMENTS

| | | | | |
|---|---|---|---|---|
| 3,645,745 A | * | 2/1972 | Magnino et al. | 530/378 |
| 4,559,222 A | | 12/1985 | Enscore et al. | 424/28 |
| 4,708,874 A | * | 11/1987 | De Haan et al. | 424/470 |
| 5,106,639 A | | 4/1992 | Lee et al. | 426/302 |
| 5,236,783 A | * | 8/1993 | Aoki et al. | 428/403 |
| 5,385,707 A | * | 1/1995 | Miltenyi et al. | 422/69 |
| 5,585,115 A | * | 12/1996 | Sherwood et al. | 424/489 |
| 5,785,984 A | * | 7/1998 | Kurihara et al. | 424/439 |
| 6,030,645 A | | 2/2000 | Tritsch et al. | 426/490 |
| 6,048,557 A | * | 4/2000 | Van Den Burg et al. | 426/99 |

FOREIGN PATENT DOCUMENTS

| | | |
|---|---|---|
| DE | 4411414 | 11/1995 |
| EP | 0424578 | 5/1991 |
| EP | 0607886 | 7/1994 |
| FR | 2758055 | 7/1998 |
| JP | 6181725 | 7/1994 |
| WO | WO 87/03899 | 7/1987 |
| WO | WO 94/01001 | 1/1994 |

OTHER PUBLICATIONS

"Silicium". Definition of "silicium" from YourDictionary.com. Accessed online on Apr. 14, 2008 at https://www.yourdictionary.com/silicium.*
"Silicon". Description of "silicon". Accessed online on Apr. 14, 2008 at http://elements.vanderkrogt.net/elem/si.html.*

* cited by examiner

*Primary Examiner* — Robert A Wax
*Assistant Examiner* — Melissa Mercier
(74) *Attorney, Agent, or Firm* — Fulbright & Jaworski L.L.P.

(57) ABSTRACT

There is provided a method of preparing an unsaturated fatty acid dry concentrate, wherein a substance comprising at least one unsaturated fatty acid is applied on a biologically inert matrix having a large surface area and is subsequently dried, as well as a composition comprising at least one unsaturated fatty acid and foods, beverages, drugs comprising this composition.

47 Claims, No Drawings

METHOD OF PREPARING AN UNSATURATED FATTY ACID DRY CONCENTRATE

The invention relates to a method of preparing an unsaturated fatty acid dry concentrate as well as a composition comprising at least one unsaturated fatty acid and food, beverages and drugs comprising said composition.

Fatty acids (alcanic acids) are structural elements of lipids, phosphoglycerides, glycolipids, cholesterol esterases and waxes. They consist of an extended, usually unbranched hydrocarbon chain and a terminal carboxyl group. The chain either is saturated or contains one or several nonconjugated cis double bindings; the latter being denoted as unsaturated fatty acids. Higher animals lack the cytochrome-$b_5$-ADPH-dependent oxygenase system required to form unsaturated fatty acids, wherefore linolic and linolenic acids belong to their essential fatty acids, i.e., their demand for such fatty acids must be met via food intake.

While, until some years ago, linolic acid (omega-6 fatty acid; C 18:2 (9,12)) was regarded as the sole value-determining factor for the supply of unsaturated fatty acids in dietary food, recent scientific findings have focused on the biological and essential importance of other unsaturated fatty acids such as, for instance, linolenic acid, stearidonic acid, oleic acid, erucic acid, nervic acid, palmitoleic acid and vaccenic acid. These (highly) unsaturated fatty acids are considered to be of a high biological and nutrition-medical relevance, in particular, in respect to prostaglandin (i.e., inflammatory) metabolism, heart and circulation, carbohydrate metabolism (diabetes), overweight, skin metabolism (neurodermitis, psoriasis), hormone metabolism, performances of the central nervous system, lungs (asthma), joints (arthritis), immune system (allergies, cancer, AIDS), autoimmune diseases, degenerative diseases of the joints, growth processes of infants and adolescents, athletes' and heavy workers' metabolisms, and aging processes. The adequate and well-balanced supply of (highly) unsaturated fatty acids is, therefore, necessary to optimize health.

Unsaturated fatty acids occur in different concentrations, primarily in unrefined vegetable oils, all of which have an oily character. Some of these oils, in particular hempseed oil, linseed oil and fish oil, in addition, have a strong, penetrating inherent smell and taste, which largely limits the wide use of such oils despite their high health values.

Another problem involved in food enriched with unsaturated fatty acids consists in that the unrefined and hence unsaturated-fatty-acid-rich oils have only a very limited storage quality and their applicability is largely reduced on account of their oily consistency. In order to avoid the above-mentioned drawbacks and produce products enriched with unsaturated fatty acids, which will also be accepted by consumers, such oils are processed in a technologically complex procedure. Due to the strict production conditions required for such processing, unsaturated fatty acids are, however, altered to such an extent that their high health values get lost. Moreover, the processing of the cited oils to common drug forms such as capsules, tablets or liquids, in turn, only insufficiently satisfies the daily demands required from a nutrition-physiological point of view, which are in the gram range, due to the dose volumes limited on account of the drug forms mentioned.

WO 87/03899 describes a method of preparing an omega-3 concentrate by esterifying the fatty acid fraction of fish oil at room temperature. After this, the alkyl ester is precipitated and separated upon heating to 55 to 90° C. and subsequent cooling to 0° C. Subsequent purification by extraction with a solvent yields the desired product. This method, however, comprises several steps in which the unsaturated fatty acids are subjected to relatively severe conditions (large temperature fluctuations, different solvents and buffers, etc.) so that a portion of the unsaturated fatty acids will be modified or lost.

U.S. Pat. No. 6,030,645 is concerned with dry particles comprising an oleophilic active substance dispersed in a carrier material, which particles are coated with a composition containing calcium silicate. The oleophilic substance is, for instance, arachidonic acid, carotenoids or the like. Cellulose, maltodextrin, alginate, lactate, gum, gelatin, sugar, sugar alcohol and starch are, inter alia, cited as carrier material examples. These particles are produced by mixing the oleophilic substance with the carrier material and spraying this mixture into calcium silicate such that the oleophilic particles formed by spraying will be coated with calcium silicate. The particles are then dried.

According to JP 6181725 A, a composition comprising a readily oxidizable oily substance is introduced into a porous carrier by pressure reduction in a manner that the composition displaces the air in this porous carrier.

FR 2 758 055 A1 relates to a powdery substance comprising oil based on unsaturated fatty acids and an absorbent, such as starch. The oil and the absorbent are homogenized and atomized in order to obtain microparticles, whereupon the water contained in those microparticles is evaporated.

U.S. Pat. No. 5,106,639 A describes a process for preparing fodder additives by mixing, and subsequently drying to powdery form, a carrier, an emulsifier and an oil containing omega-3 fatty acids. The carrier may be, for instance, soybean protein, starch, pectin, gelatin, collagen, casein and the like.

EP 0 424 578 A1 refers to a dry mixture comprising an oil containing unsaturated fatty acids and caseinate, whereby these two substances are mixed together, whereupon the composition is dried.

DE 4 411 414 C1 describes a product for enterally feeding fatty acids and/or amino acids as well as a method of preparing such a product by incorporating said fatty acids into the amylose helix by extrusion along with starch so as to form inclusion complexes. After this, the mass may be dried.

U.S. Pat. No. 4,559,222 A discloses a composition comprising a drug, which composition further includes a mineral oil and silicon dioxide.

All of the methods described above involve, however, the drawback that high-quality oils having high portions of unsaturated fatty acids are treated without sufficient care so that too high a portion of unsaturated fatty acids will be lost in the course of the method.

It is the object of the present invention to provide a method for preparing a concentrate of unsaturated fatty acids, in which the above-mentioned drawbacks are avoided and by which the high health values of unsaturated fatty acids will be preserved, nevertheless. Such a concentrate is to provide doses including sufficient quantities of unsaturated fatty acids without the latter having too large a volume. The method is to ensure a fine surface distribution of the oil particles and the precise dosability of the quantitative ratios of fatty acids to carrier matrix.

The method according to the invention, of the initially defined kind is characterized in that a substance comprising at least one unsaturated fatty acid is applied on a biologically inert matrix having a large surface area and is subsequently dried. In the context of the present invention, "substance" is meant to encompass an oil, preferably an untreated oil, as well as any composition comprising at least one unsaturated fatty acid. By applying the substance on a biologically inert matrix having a large surface area, it is ensured that the substance is distributed as intensively as possible in a volume as small as possible. It is, thus, feasible to dry the substance rapidly and under mild conditions and provide the same in high concentrations stable in storage. In doing so, it is important that the matrix be biologically inert, thus avoiding any vulnerability or modification of the unsaturated fatty acid(s). The unsaturated fatty acids adhere to the matrix, thus being 1) readily handleable and 2) protected to some degree by the matrix, against substances attacking unsaturated fatty acids. In order to enable a good distribution and sufficient drying of the unsaturated fatty acids, it is important that the biologically inert matrix has a large surface area, i.e., a surface area of 50-1000 $m^2/g$.

Within the context of the present invention, by a matrix having a "large surface area", a carrier is to be understood that is highly disperse. The application of fatty acids on the highly disperse matrix, for instance by spraying, causes fine fatty acid droplets to attach to the finely distributed matrix particles. This ensures a perfectly fine surface distribution of the fatty acid particles as well as the precise dosability of the quantitative ratios of fatty acids and carrier matrix. In this manner, it has become possible for the first time to concentrate and dry the temperature and oxygen sensitive fatty acids gently and without any losses, or at a minimal loss only. Unlike porous carrier materials according to the prior art, the highly disperse matrix yields a dry and highly concentrated fatty acid product. Thus, high-quality oils such as high-quality vegetable oils containing high portions of thermally unstable and oxygen-sensitive fatty acids will be united with the matrix and dried under mild temperature conditions.

Preferably, the matrix has an average surface area of at least 100 $m^2/g$, particularly preferred at least 150 $m^2/g$, even more preferred at least 200 $m^2/g$, most preferably at least 400 $m^2/g$.

The average particle size of the matrix is, for instance, approximately 900 nm at most, preferably 500 nm at most, particularly preferred 250 nm at most, 100 nm at most, 50 nm at most, 25 nm at most and, most preferred, 15 nm at most.

The combination of the application of the unsaturated fatty acids on the biologically inert matrix and subsequent drying ensures the provision of a dry concentrate comprising unsaturated fatty acids without exhibiting an oily consistency and a penetrating inherent smell and taste. Moreover, the storage quality has been substantially enhanced. In addition, the preparation method according to the invention may be carried out in a quick and cost-effective manner. Finally, the compositions according to the invention are readily apt for further food technological processing.

Another advantage consists in that practically no loss of unsaturated fatty acids is involved, as is the case with common methods such as, for instance, extraction methods.

It is particularly favorable, if the substance is applied on the matrix through jet nozzles. This ensures a fine distribution of the substance already prior to its application on the matrix, thus safeguarding a uniform fine distribution on the matrix.

In order to ensure thorough blending, it is beneficial if the matrix—fatty acid mixture is blended in a mixing device, in particular by the aid of a mixing screw. In doing so, any prior art mixing device (including a mixing screw) may be employed, whereby the mixing vessel ought to be completely sealable. It is advantageous if vibrating means are additionally attached to the vessel wall to promote the mixing in of raw materials difficult to blend. The mixing accuracy may, furthermore, be increased by tilting and rocking movements of the mixing vessel. When using shearing heads, the mixture will become even finer and lumps and agglomerates that might form within the mixing mass will be disintegrated. In doing so, it is beneficial if parameters such as the mixing time, injection time, injection pressure, tilting angle, vibrators and shearing head connections are programmable and adjustable. This facilitates process optimization by those skilled in the art of food technology in respect to any substance and surface. An example of a suitable mixing device is the batch mixer "Prodima AC-LI/500".

In order to ensure uniform and gentle, yet rapid drying, it is advantageous if the matrix—fatty acid mixture is vacuum dried. Thus, relatively gentle operating conditions may be applied. Vacuum drying is well known to the skilled artisan. During vacuum drying, the mixture may be constantly agitated, for instance in a vat, by the aid of an agitating means. The vapour formed by vacuum drying may be condensed by the aid of a condenser and diverted into a water reservoir. The vat preferably is arranged rotatably and horizontally and may have any capacity, for instance 500 to 1000 liters. In a preferred manner, the device is temperature and/or pressure-controlled.

A particularly favorable way of drying is characterized in that the matrix—fatty acid mixture is dried at 1-50 mbars, in particular at 10-30 mbars. Such a vacuum safeguards gentle drying without temperature impairment.

In doing so, it is particularly advantageous if the matrix—fatty acid mixture is dried at 10 to 50° C., in particular 30 to 36° C. Within that operating range, no damage to the unsaturated fatty acids will occur. The vat is heated to a constant temperature, for instance, by a control means. To this end, the drum may be provided with a double-walled jacket for hot water which is heated by the heat recovered from the cooling aggregate. Furthermore, a continuous flow heater may be additionally installed to produce additional heat.

Preferably, the substance is applied on a silicon matrix, for instance an $SiO_2$ matrix. Such a matrix from a biological point of view is absolutely inert and has a sufficiently large surface area in order to provide for a matrix that is beneficial to the method.

It is particularly favorable if the substance is applied on a matrix prepared of Silicium dioxydatum dispersum. Such a matrix is particularly suitable for the application of unsaturated fatty acids and subsequent drying.

The matrix is produced, for instance, of Aerosil®, a highly disperse silicic acid containing more than 99.8% $SiO_2$. This matrix is made of amorphous spherical particles having diameters of approximately 10 to 20 nm. At a volume of about 15 ml, 1 g Aerosil® has a surface area of 100 to 400 $m^2$. This matrix is particularly suitable for the method according to the invention.

A particularly advantageous method is characterized in that linseed oil, safflower oil, borage oil, hempseed oil, soybean oil, bumpkin seed oil, sunflower oil, sesame seed oil, evening primrose oil and/or fish oil are applied on the matrix as said substance. These oils comprise different concentrations of (highly) unsaturated fatty acids (cf. Tables 1 to 3). If these vegetable oils are applied on the matrix in the natural state, they will exhibit extremely high health values because of their contents of unsaturated fatty acids. Moreover, the method is, thus, realized in a rapid and cost-effective manner.

Preferably, a substance comprising (highly) unsaturated fatty acids, in particular omega-3, omega-6, omega-7 and/or omega-9 fatty acids is applied on the matrix. It is feasible to use either individual purified fatty acids or also a mixture of two or more of these fatty acids. Furthermore, a vegetable oil comprising such fatty acids may be used as well.

A particularly advantageous method is characterized in that 1 to 3, in particular 1.5, parts by weight of the substance per part by weight of the matrix are applied on the matrix. Thus, a perfect unsaturated fatty acid to matrix ratio will be achieved with the maximum amount of fatty acid being applied on the matrix quantity required therefor and as large a surface as possible per as small a volume as possible of fatty acid dry concentrate being obtained.

In order to obtain a product having a maximum storage quality, it is favorable if the matrix—fatty acid mixture is supplemented with at least one stabilizer, in particular an antioxidant. D,L-alpha-tocopherol and ascorbyl palmitate are suitable stabilizers, in particular, for highly unsaturated fatty acids. Thereby, the storage quality of the dry concentrate will be enhanced and its stability will be improved, in particular with a view to further processing.

Furthermore, it is particularly preferred if at least one odor and/or taste corrective is added to the matrix—fatty acid mixture. In this manner, any possibly remaining unpleasant smell or taste of the unsaturated fatty acids will be suppressed. In the context of the present invention, by odor and taste corrective not only the masking of an unpleasant smell or taste is meant, but also the introduction of a pleasant smell or taste, for instance, by a sweetening agent, fruit aroma, essential oils, etc.

In doing so, it is particularly favorable if Etheroleum citri is added as said odor or taste corrective. This is particularly apt for the addition to unsaturated fatty acids.

Another advantageous method is characterized in that the matrix—fatty acid mixture is supplemented with milk, in particular pasteurized milk, prior to drying. Any milk may be added, in particular cow's milk, mare's milk, asses' milk, colostral milk, goat's milk and/or ewe's milk. Dry concentrates of the milk species mentioned, or fractions of the same, inter alia, have immunostimulating effects on human and animal organisms. By the addition of (highly) unsaturated fatty acids, the contents of such essential nutrients in milk concentrates may be quantitatively raised according to demands, thus enhancing the biological values of milk concentrates.

Preferably, 1 to 2, in particular approximately 1.5, parts by weight of milk are added per part by weight of matrix—fatty acid mixture. This quantitative ratio has proved to be particularly favorable, whereby the advantages of the addition of milk will be obtained without disturbing the further drying process or adversely affecting the unsaturated fatty acids.

Concerning the ingestion of such concentrates, it is particularly beneficial if the matrix—fatty acid mixture is further processed after drying, in particular, to form powders, capsules, tablets or liquids. In doing so, further additives such as, e.g., vitamins, flavours, minerals, drugs, etc. may also be added. Moreover, it is, for instance, feasible to prepare the necessary daily doses of unsaturated fatty acids in unit forms such as tablets or capsules.

In doing so, it is particularly preferred if the matrix—fatty acid mixture after drying is added to foods and/or beverages, in particular baby food, milk products and/or baking mixtures. Since the fatty acid dry concentrate does not have an oily consistency, nor an unpleasant smell or taste, its addition will not substantially modify the respective foodstuff or beverage such that no, or hardly any, additional method steps are required.

According to another aspect, the present invention refers to a composition comprising at least one unsaturated fatty acid and a matrix having a large surface area. Concerning the unsaturated fatty acids and matrix, the same as pointed out above applies also in this case, whereby the composition is preferably a concentrate of at least one unsaturated fatty acid. This composition may have any conceivable consistency, yet it is preferably made available as a dry concentrate. Due to the combination of unsaturated fatty acid with a matrix having a large surface area, the composition surprisingly does not have the oily consistency usually met with current unsaturated-fatty-acid-comprising products. Besides, this composition does not have the otherwise occurring penetrating inherent smell and taste and offers an extremely long shelf life, in particular in the dry concentrate form.

Preferably, the matrix is a silicon matrix, for instance an $SiO_2$ matrix, in particular a Silicium dioxydatum dispersum-matrix. Such a matrix is particularly suitable as an inert basic substance of an essential-fatty-acid-comprising composition, has a large surface area and is particularly well suited for any further processing.

Preferably, the composition comprises linseed oil, safflower oil, borage oil, hempseed oil, soybean oil, bumpkin seed oil, sunflower oil, sesame seed oil, evening primrose oil and/or fish oil. These oils have high contents of (highly) unsaturated fatty acids and, in particular in the unrefined state, exhibit high health values.

It is particularly favorable if the composition comprises at least one (highly) unsaturated fatty acid, in particular omega-3, omega-6, omega-7 and/or omega-9 fatty acids. These essential fatty acids are of particular relevance to various biochemical processes and also to the building up of vital substances.

Advantageously, the composition comprises 0.1 to 3 parts by weight of the at least one unsaturated fatty acid per part by weight of the matrix. It goes without saying that the concentration and also the type of the unsaturated fatty acid will more or less strongly vary if an unrefined oil is used to prepare the composition. This ratio, which depends, of course, also on the respective further processing envisaged, usually is the optimum ratio, anyway.

Preferably, the composition comprises at least one stabilizer, in particular an antioxidant, at least one odor and/or taste corrective, in particular Etheroleum citri, and/or dried milk, in particular pasteurized milk. These additives will optimize the properties of the composition, facilitate further processing of the same and exert particularly beneficial influences on the end product, for instance, in terms of storage quality and taste.

A particularly favorable composition is characterized in that it comprises 1 to 2, in particular 1.5, parts by weight of milk per part by weight of the matrix—fatty acid mixture. Thus, the optimum consistency will be achieved.

In order to ensure good storage qualities and facilitate further processing, it is preferred that the composition be dried. Compositions according to the invention having $A_W$ values of below 0.8 are particularly preferred.

A further aspect of the present invention is the provision of a food, beverage or drug which is characterized in that it is supplemented with a composition according to the invention as described above. The food or beverage may be any commercially available product, for instance a staple food or a semiluxury. The consistency of the food is not critical, it may be both liquid, e.g., a fruit juice, viscous such as a yoghurt, jam, oil, etc., or solid such as a baking mixture, muesli or the like. It goes without saying that the composition may be made available also in a highly concentrated form as an effervescent tablet, syrup or the like. Also the drug comprising the composition according to the invention may be of any conceivable form and consistency, for instance, a tablet, liquid, powder or capsule.

In the following, the method according to the invention will be explained in more detail by way of the following Example, to which, however, it is not limited.

EXAMPLE

In a mixer of the trademark Prodima "Batch-Mischer Prodima AC-LI/500", in which Silicium dioxydatum dispersum has been previously charged, the following components are injected into the injection equipment through fine jet nozzles under constant stirring:
- linseed oil: 2 parts by weight (cf. Table 1)
- safflower oil: 1 part by weight (cf. Table 2)
- borage oil: 1 part by weight (cf. Table 3)
- D,L-alphatocopherol and ascorbyl palmitate as stabilizers
- odor and taste correctives (Etheroleum citri)

TABLE 1

| Linseed oil (g fatty acids/100 g fat) | |
|---|---|
| Palmitic acid | 5.95 |
| Stearic acid | 3.60 |
| Oleic acid | 18.20 |
| Linolic acid | 13.90 |
| Linolenic acid | 54.20 |

TABLE 2

| Safflower oil—Fatty acid composition % (subject to fluctuations) | |
|---|---|
| C14:0 | 0.1-0.2 |
| C14:1 | 0 |
| C16:0 | 6.7-7.7 |
| C16:1 | 0 |
| C18:0 | 2.4-2.7 |
| C18:1 | 12.6-13.6 |
| C18:2 | 75.7-77.1 |
| C18:3 | 0-0.2 |
| C20:0 | 0.3-0.4 |
| C20:1 | 0-0.2 |
| C22:0 | 0-0.2 |
| C22:1 | 0 |
| C24:0 | 0 |

TABLE 3

| Borage oil | |
|---|---|
| Acid value (mg KOH/oil) | 0.1% |
| gamma linolenic acid content | 23.6% |

Based thereon, the silicon dioxide previously charged into the mixing device comprises 2.7 parts by weight. The thus obtained EFS powder (EFS=essential fatty acids) contains an overall portion of essential fatty acids of 48.3% according to the following distribution pattern:

TABLE 4

| omega-3 fatty acids: | |
|---|---|
| C 18:3 (9, 12, 15) alpha-linolenic acid | 10.5% |
| C 18:4 (4, 8, 12, 15) stearidonic acid | 0.01% |
| omega-6 fatty acids: | |
| C 18:2 (9, 12) linolic acid | 16.8% |
| C 18:3 (6, 9, 12) gamma-linolenic acid | 2.5% |
| omega-9 fatty acids: | |
| C 18:1 (9) oleic acid | 7.8% |
| C 22:1 (13) erucic acid | 0.3% |
| C 24:1 (15) nervonic acid | 0.12% |
| omega-7 fatty acids: | |
| C 16:1 (9) palmitoleic acid | 0.02% |
| C 18:1 (11) vaccenic acid | 0.05% |

Approximately 41 kg EFS concentrate were precharged into an evaporation apparatus "mare's milk device". After this, approximately 57 kg pasteurized milk (optionally cow's, mare's, asses', colostral, goat's or ewe's milk) were added and evaporated for 24 hours at a temperature of 32° C. and under vacuum conditions (about 10 mbars). After 24 hours, the aqueous portion of the added milk had been evaporated under mild temperature conditions. The residue obtained by this method was a milk—EFS concentrate having a high portion of (highly) unsaturated fatty acids in a stable, organoleptically acceptable and highly concentrated powder form. This powder form may be further processed to various products (baking mixtures, baby food, milk products) and also to various drug forms such as capsules, tablets, etc.

The invention claimed is:

1. A method of increasing stability of an unsaturated fatty acid comprising:
   preparing a matrix/fatty acid mixture by applying a substance comprising at least one unsaturated fatty acid to a non-porous biologically inert matrix having a large surface area of from 100 to 1000 m$^2$/g; and
   drying the matrix/fatty acid mixture to prepare an unsaturated fatty acid dry concentrate; wherein stability of the fatty acid is increased.

2. The method of claim 1, wherein the substance is applied to the matrix through at least one jet nozzle.

3. The method of claim 1, wherein the matrix/fatty acid mixture is blended in a mixing device.

4. The method of claim 3, wherein the matrix/fatty acid mixture is blended with the aid of a mixing screw.

5. The method of claim 3, wherein the matrix/fatty acid mixture is vacuum-dried.

6. The method of claim 5, wherein the matrix/fatty acid mixture is dried at 1-50 mbar.

7. The method of claim 6, wherein the matrix/fatty acid mixture is dried at 10-30 mbars.

8. The method of claim 5, wherein the matrix/fatty acid mixture is dried at 10 to 50° C.

9. The method of claim 8, wherein the matrix/fatty acid mixture is dried at 30 to 36° C.

10. The method of claim 1, wherein the matrix is defined as a silicon matrix.

11. The method of claim 10, wherein the matrix is further defined as a Silicium dioxydatum dispersum-matrix.

12. The method of claim 1, wherein the substance comprises linseed oil, safflower oil, borage oil, hempseed oil, soybean oil, bumpkin seed oil, sunflower oil, sesame seed oil, evening primrose oil, and/or fish oil.

13. The method of claim 1, wherein the substance comprises at least one highly unsaturated fatty acid.

14. The method of claim 13, wherein the at least one highly unsaturated fatty acid is an omega-3, omega-6, omega-7, or omega-9 fatty acid.

15. The method of claim 1, wherein 1 to 3 parts by weight of said substance per part by weight of said matrix are applied on said matrix.

16. The method of claim 15, wherein 1.5 parts by weight of said substance per part by weight of said matrix are applied on said matrix.

17. The method of claim 1, wherein at least one stabilizer is further added to the matrix/fatty acid mixture.

18. The method of claim 17, wherein the at least one stabilizer is an antioxidant.

19. The method of claim 1, wherein at least one odor and/or taste corrective is further added to the matrix/fatty acid mixture.

20. The method of claim 19, wherein the odor and/or taste corrective is Etheroleum citri.

21. The method of claim 1, wherein milk is added to the matrix/fatty acid mixture prior to drying.

22. The method of claim 21, wherein the milk is pasteurized milk.

23. The method of claim 21, wherein 1 to 2 parts by weight of milk are added per part by weight of the matrix/fatty acid mixture.

24. The method of claim 23, wherein 1.5 parts by weight of milk are added per part by weight of the matrix/fatty acid mixture.

25. The method of claim 1, wherein after drying, the matrix/fatty acid mixture is further processed to form powders, capsules, tablets or liquids.

26. The method of claim 1, wherein after drying, the matrix/fatty acid mixture is added to a food and/or beverage.

27. The method of claim 26, wherein the food and/or beverage is a baby food, milk product, and/or baking mixture.

28. A composition comprising at least one unsaturated fatty acid and a non-porous biologically inert matrix having a large surface area of from 100 to 1000 $m^2/g$, wherein the unsaturated fatty acid has increased stability relative to the same fatty acid not bound to the matrix.

29. The composition of claim 28, wherein the matrix is a silicon matrix.

30. The composition of claim 29, wherein the matrix is a Silicium dioxydatum dispersum-matrix.

31. The composition of claim 28, further defined as comprising linseed oil, safflower oil, borage oil, hempseed oil, soybean oil, bumpkin seed oil, sunflower oil, sesame seed oil, evening primrose oil and/or fish oil.

32. The composition of claim 28, further defined as comprising at least one highly unsaturated fatty acid.

33. The method of claim 32, wherein the at least one highly unsaturated fatty acid is an omega-3, omega-6, omega-7, or omega-9 fatty acid.

34. The composition of claim 28, further defined as comprising 0.1 to 3 parts by weight of said at least one unsaturated fatty acid per part by weight of said matrix.

35. The composition of claim 28, further defined as comprising at least one stabilizer.

36. The composition of claim 35, wherein the at least one stabilizer is an antioxidant.

37. The composition of claim 28, further comprising at least one odor and/or taste corrective.

38. The composition of claim 37, wherein the at least one odor and/or taste corrective is Etheroleum citri.

39. The composition of claim 28, further defined as comprising dried milk.

40. The composition of claim 39, wherein the dried milk is dried pasteurized milk.

41. The composition of claim 39, further defined as comprising 1 to 2 parts by weight of milk per part by weight of the matrix/fatty acid mixture.

42. The composition of claim 41, further defined as comprising 1.5 parts by weight of milk per part by weight of the matrix/fatty acid mixture.

43. The composition of claim 28, wherein the composition is dry.

44. The composition of claim 28, wherein the composition is comprised in a food.

45. The composition of claim 28, wherein the composition is comprised in a beverage.

46. The composition of claim 28, wherein the composition is comprised in a drug.

47. The method of claim 8, wherein the matrix/fatty acid mixture is dried at 30 to 50° C.

* * * * *

UNITED STATES PATENT AND TRADEMARK OFFICE
CERTIFICATE OF CORRECTION

PATENT NO. : 8,052,991 B2
APPLICATION NO. : 10/312077
DATED : November 8, 2011
INVENTOR(S) : Norbert Fuchs et al.

It is certified that error appears in the above-identified patent and that said Letters Patent is hereby corrected as shown below:

In title page, item (30) Foreign Application Priority Data, insert
--June 20, 2000  (AT)  ............  A 1063/2000--.

Signed and Sealed this
Third Day of January, 2012

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 8,052,991 B2 | Page 1 of 1 |
| APPLICATION NO. | : 10/312077 | |
| DATED | : November 8, 2011 | |
| INVENTOR(S) | : Fuchs et al. | |

It is certified that error appears in the above-identified patent and that said Letters Patent is hereby corrected as shown below:

In title page, item (73) Assignee, delete "VIS-Vitalis Linzenz-Und Handels GmbH" and insert --vis-vitalis Lizenz- und Handels GmbH-- therefor.

Signed and Sealed this
Thirteenth Day of March, 2012

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 8,052,991 B2 | Page 1 of 1 |
| APPLICATION NO. | : 10/312077 | |
| DATED | : November 8, 2011 | |
| INVENTOR(S) | : Fuchs et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1953 days.

Signed and Sealed this
Seventeenth Day of June, 2014

Michelle K. Lee
*Deputy Director of the United States Patent and Trademark Office*